United States Patent [19]

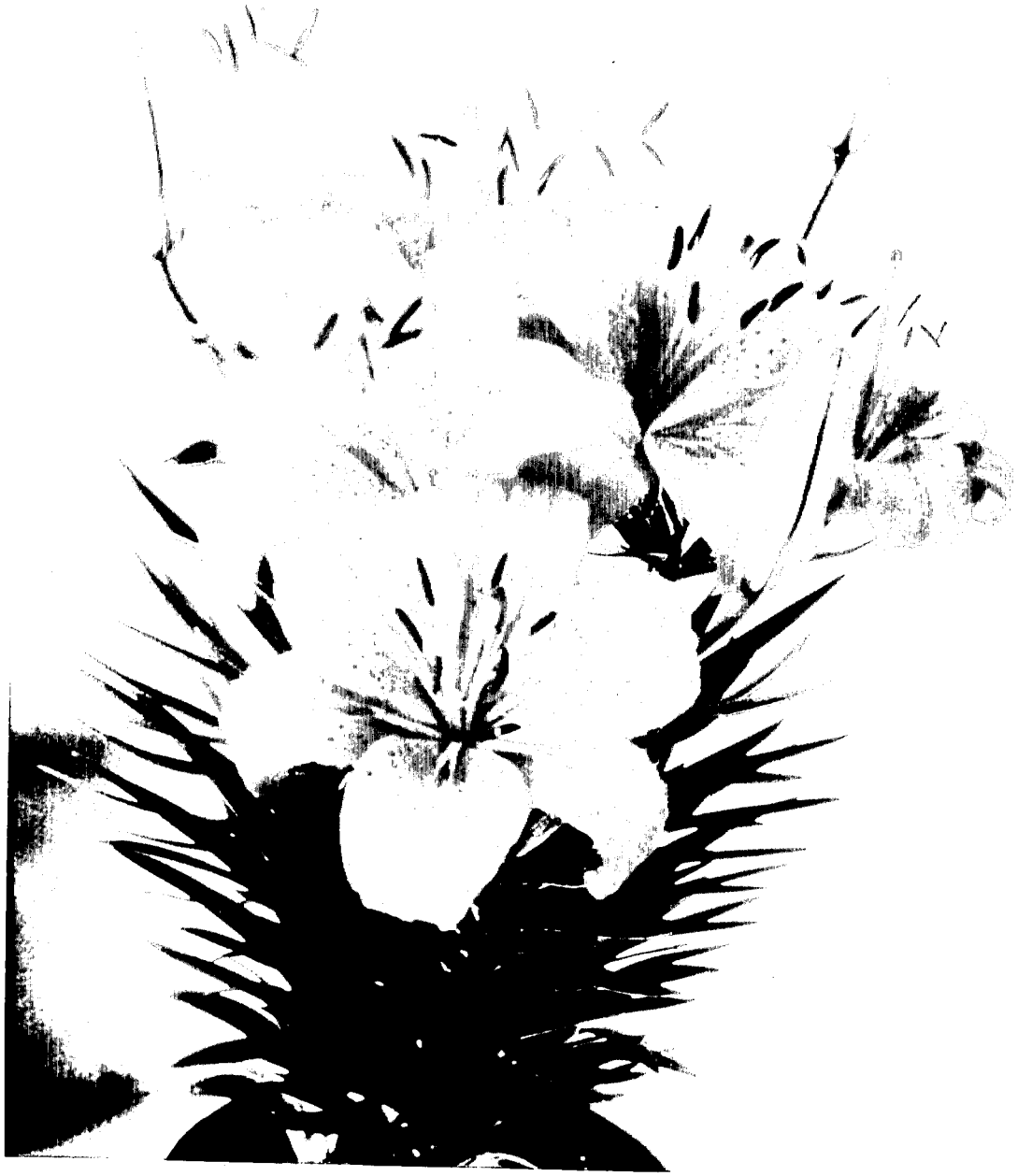

McRae

[11] Patent Number: Plant 5,792

[45] Date of Patent: Oct. 21, 1986

[54] LILY PLANT NAMED ORANGE PIXIE

[75] Inventor: Edward A. McRae, Boring, Oreg.

[73] Assignee: Melridge Inc., Sandy, Oreg.

[21] Appl. No.: 659,238

[22] Filed: Oct. 9, 1984

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Chas. W. Rummler; John B. Lungmus

[57] ABSTRACT

A new hybrid Asiatic lily plant of the chalice type bearing large clusters of medium sized flowers of strong color, excellent form and long persistence, both on the plant and as potted plants, this plant being distinguished by having reddish stems and excellent foliage, the flowers having broad petals of fine substance, the buds displaying an orange color prior to opening and the flowers being characterized by a rich brilliant orange color which is very lightly spotted.

1 Drawing Figure

BACKGROUND OF THE NEW PLANT

My new lily cultivar originated as a seedling selected from a group of seedlings produced at Sandy, Oreg., and resulting from my crossing of the variety "Harmony"×"Sunspot" (unpatented), as the seed parent, with the variety "Charisma" (U.S. Plant Pat. No. 4,180), as the pollen patent, my objective being to produce upright Asiatic lilies in the orange color range which have a high tolerance to virus infection, reliability and rapidity of forcing performance. This particular seedling was selected for propagation because of its single, strong, reddish stem with abundant foliage of deep green color, and its excellent flower form with broad petals of fine substance and a brilliant orange color which persists over a long period of time.

This selected seedling was asexually propagated by me and under my direction through successive generations at Sandy, Oreg., by bulb scale techniques and by means of bulblets and this propagation has demonstrated that the novel characteristics derived from the original seedling hold true from generation to generation and appear to be firmly fixed.

DESCRIPTION OF THE DRAWING

My new Asiatic lily cultivar is illustrated by the accompanying photographic drawing which shows in full color the foliage, buds, and a fully opened flower, the color rendition being as nearly true as can be reasonably obtained by conventional photographic procedures.

DESCRIPTION OF THE NEW VARIETY

The following is a detailed description of my new lily cultivar as observed at Sandy, Oreg., with color designations according to The R.H.S. Colour Chart and with nomenclature according to the International Lily Register (Royal Horticultural Society, London, England, 2nd edition, 1969).

THE PLANT

Origin: Seedling.

Parentage:

*Seed parent.*—Harmony×Sunspot (unpatented).

*Pollen parent.*—Charisma (U.S. Plant Pat. No. 4,180).

Classification:

*Botanic.*—Hybrid lily cultivar; Division 1-A of the Horticultural Classification of Lilies of The Royal Horticultural Society of London, England.

*Commercial.*—Asiatic hybrid lily.

Form: Single stem from each bulb, erect and stately.

Height: 35 to 42 cm. from bulbs 12 to 14 cm. in circumference.

Growth: Vigorous, sturdy and upright.

Stem color: Reddish, produced by red pigment over green.

Strength: Excellent.

Foliage:

*Quantity.*—Abundant.

*Size of leaf.*—8 to 9 cm. long.

*Shape of leaf.*—Broad ensiform.

*Aspectl*—Glossy.

*Color.*—Upper and under sides, deep green.

Bulbs:

*Color* Varying with age, ranging up to 30 cm. in circumference.

*Color.*—White.

THE BUD

Form: Obtuse, urn-shaped and long.

Size: About 5 to 7 cm. long and about 9 cm. in circumference at maturity.

Opening rate: The bud opens slowly.

Color: Deep orange when outer tepals first divide becoming deep golden orange when tepals begin to unfurl.

Tepals: Bright orange on the inside and deep reddish orange on the outside.

Peduncle:

*Length.*—About 4 cm., erect and deep green in color.

THE FLOWER

Blooming habit: Annually in early summer. This plant blooms once and profusely each year.

Size of bloom: Medium; 14 to 18 cm. in diameter.

Borne: In clusters, from 3 to 7 on a single stem from a bulb 12 to 14 cm. in diameter.

Shape: Chalice, with tepals spreading generally flat and without substantial change in form with age.

Tepalage:

*Number of tepals.*—Six.

*Shape.*—Very broad, inner tepals being 3 to 5 cm. wide.

*Arrangement.*—Normal.

*Color.*—Brilliant orange, R.H.S. 30A, on both the outer and inside portions of the tepal. The midrib is about 1 cm. wide and extends from the nectary to the tepal tip, the color being R.H.S. 21A on a newly opened flower and as the flower ages, 4 to 6 days, the midrib color deepens to R.H.S. 23A. The reverse side of the tepal is a somewhat deeper orange in color than the upper side and the general color of the flower changes to a slightly richer color after full bloom.

Aspect: The appearance of the tepals is satiny.

Pedicel:

*Length.*—About 7 to 10 cm.

*Color.*—Deep green.

*Form.*—The pedicel is sturdy and upright.

Fragrance: The flower is not fragrant.

Disease resistance: The plant and flower are resistant to disease; in particular, they are resistant to Fusarium and Botrytis as observed where grown in Oregon.

Persistence: The flowers are very long lasting both on the plant and as potted plants.

THE REPRODUCTIVE ORGANS

Stamens:

*Arrangement.*—Typical of Liliaceae.

*Length.*—About 5 cm.

*Number.*—Six.

*Filaments.*—5 cm. in length and reddish brown in color.

*Anthers and pollen.*—Reddish brown in color.

Pistils: One in number with a length of about 5 cm.

*Stigma.*—Deepest purple maroon in color.

Ovaries: Typical of genus Lilium.

FRUIT

Fertility: The fruit is fertile.

Shape: Ovoid.

Color at maturity: Soft brown.

This new lily most closely resembles the lily cultivar "Harmony" but is distinguished therefrom by its shorter stature and flower form, and the brighter orange color of its flowers.

I claim:

1. A new and distinct variety of hybrid Asiatic lily, substantially as herein shown and described, characterized by its single stem of reddish color, its abundant deep green foliage, and the brilliant orange color of the tepals when the flower is in bloom.

* * * * *